US00PP26225P2

(12) United States Plant Patent
Geibel

(10) Patent No.: US PP26,225 P2
(45) Date of Patent: Dec. 15, 2015

(54) *PELARGONIUM* PLANT NAMED 'REGBESOPI'

(50) Latin Name: *Pelargonium grandiflorum*
Varietal Denomination: REGBESOPI

(71) Applicant: Martin Geibel, Dresden (DE)

(72) Inventor: Martin Geibel, Dresden (DE)

(73) Assignee: Elsner pac Jungpflanzen Gbr, Dresden (DE)

( * ) Notice: Subject to any disclaimer, the term of this patent is extended or adjusted under 35 U.S.C. 154(b) by 200 days.

(21) Appl. No.: 13/998,288

(22) Filed: Oct. 18, 2013

(51) Int. Cl.
*A01H 5/02* (2006.01)

(52) U.S. Cl.
USPC ..... Plt./331

(58) Field of Classification Search
USPC ..... Plt./331
See application file for complete search history.

*Primary Examiner* — June Hwu
(74) *Attorney, Agent, or Firm* — C. A. Whealy

(57) ABSTRACT

A new and distinct Regal Geranium plant named 'REGBESOPI', characterized by its upright and uniformly rounded plant habit; vigorous growth habit; freely basal branching habit; early and freely flowering habit; light pink-colored flowers with white-colored centers that are held above the foliar plane on strong peduncles; and no requirement for cooling treatment for flower development.

1 Drawing Sheet

Botanical designation: *Pelargonium grandiflorum.*
Cultivar denomination: 'REGBESOPI'.

BACKGROUND OF THE INVENTION

The present invention relates to a new and distinct cultivar of Regal Geranium plant, botanically known as *Pelargonium grandiflorum,* and hereinafter referred to by the name 'REGBESOPI'.

The new Regal Geranium plant is a product of a planned breeding program conducted by the Inventor in Dresden, Germany. The objective of the breeding program is to develop new early flowering Regal Geranium plants with unique and attractive flower types and colors.

The new Regal Geranium plant originated from a cross-pollination made by the Inventor in Dresden, Germany during the summer of 2009 of two unnamed proprietary selections of *Pelargonium grandiflorum,* not patented. The new Regal Geranium plant was discovered and selected by the Inventor as a flowering plant from within the progeny of the stated cross-pollination in a controlled greenhouse environment in Dresden, Germany during the spring of 2011.

Asexual reproduction of the new Regal Geranium plant by vegetative terminal cuttings in a controlled greenhouse environment in Dresden, Germany since October, 2011 has shown that the unique features of this new Regal Geranium plant are stable and reproduced true to type in successive generations.

SUMMARY OF THE INVENTION

Plants of the new Regal Geranium have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'REGBESOPI'. These characteristics in combination distinguish 'REGBESOPI' as a new and distinct Regal Geranium plant:

1. Upright and uniformly rounded plant habit.
2. Vigorous growth habit.
3. Freely basal branching habit.
4. Early and freely flowering habit.
5. Light pink-colored flowers with white-colored centers that are held above the foliar plane on strong peduncles.
6. No cooling treatment required for flower development.

Plants of the new Regal Geranium differ primarily from plants of the parent selections in flower coloration. In addition, plants of the new Regal Geranium are more uniform than plants of the parent selections.

Plants of the new Regal Geranium can be compared to plants of *Pelargonium grandiflorum* 'REGBEPI', disclosed in a U.S. Plant patent application Ser. No. 13/998,292 filed concurrently. In side-by-side comparisons conducted in Dresden, Germany, plants of the new Regal Geranium differed from plants of 'REGBEPI' in the following characteristics:

1. Plants of the new Regal Geranium were taller and broader than plants of 'REGBEPI'.
2. Plants of the new Regal Geranium were more vigorous than plants of 'REGBEPI'.
3. Plants of the new Regal Geranium had larger leaves than plants of 'REGBEPI'.
4. Petals of plants of the new Regal Geranium were not as undulate as petals of plants of 'REGBEPI'.
5. Plants of the new Regal Geranium and 'REGBEPI' differed in flower color as plants of 'REGBEPI' had darker pink-colored flowers.

BRIEF DESCRIPTION OF THE PHOTOGRAPH

The accompanying colored photograph illustrates the overall appearance of the new Regal Geranium plant showing the colors as true as it is reasonably possible to obtain in colored reproductions of this type. Colors in the photograph may differ slightly from the color values cited in the detailed botanical description which accurately describe the colors of the new Regal Geranium plant.

The photograph comprises a side perspective view of a typical flowering plant of 'REGBESOPI' grown in a container.

DETAILED BOTANICAL DESCRIPTION

The aforementioned photograph and following observations, measurements and values describe plants grown in 19-cm containers during the winter, spring and summer in a glass-covered greenhouse in Dresden, Germany and under cultural practices typical of commercial Regal Geranium production. During the production of the plants, day temperatures averaged 18° C., night temperatures averaged 16° C. and light levels ranged from 15 kilolux to 100 kilolux. To enhance the overall plant habit, plants were exposed to eight weeks of 9° C. day and night temperatures; however, traditional cooling treatments are not required for flower initiation and development. Plants were six months old when the photograph was taken and nine months old when the detailed description was taken. In the detailed description, color references are made to The Royal Horticultural Society Colour Chart, 1995 Edition, except where general terms of ordinary dictionary significance are used.

Botanical classification: *Pelargonium grandiflorum* 'REGBESOPI'.

Parentage:

*Female, or seed, parent.*—Unnamed proprietary selection of *Pelargonium grandiflorum,* not patented.

*Male or pollen parent.*—Unnamed proprietary selection of *Pelargonium grandiflorum,* not patented.

Propagation:

*Type.*—By vegetative terminal cuttings.

*Time to initiate roots, summer.*—About 18 days at temperatures about 20° C.

*Time to initiate roots, winter.*—About 22 days at temperatures about 20° C.

*Time to produce a rooted young plant, summer and winter.*—About four weeks at temperatures about 20° C.

*Root description.*—Fine, fibrous; white in color.

*Rooting habit.*—Freely branching; dense.

Plant description:

*Plant and growth habit.*—Upright and uniformly rounded plant habit; inverted triangle; densely foliated; vigorous growth habit; freely basal branching habit with numerous lateral branches developing per plant.

*Plant height, to top of umbels.*—About 35 cm.

*Plant height, to top of foliar plane.*—About 30 cm.

*Plant width.*—About 50 cm.

*Lateral branches.*—Length: About 20 cm. Diameter: About 5 mm. Internode length: About 1.5 cm. Texture: Pubescent. Color: Close to 144A.

Leaf description:

*Arrangement.*—Alternate or opposite; simple.

*Length.*—About 5 cm.

*Width.*—About 8.5 cm.

*Shape.*—Roughly cordate.

*Apex.*—Acute.

*Base.*—Cordate, open.

*Margin.*—Bi-serrate.

*Venation pattern.*—Palmate.

*Texture, upper and lower surfaces.*—Sparsely pubescent; leathery.

*Color.*—Developing and fully expanded leaves, upper surface: Close to 138A; venation, close to 137A. Developing and fully expanded leaves, lower surface: Close to 147B; venation, close to 144A. Zonation pattern: Not observed.

*Petioles.*—Length: About 3.5 cm. Diameter: About 2 mm. Texture, upper and lower surfaces: Smooth. Color, upper and lower surfaces: Close to 144A.

Flower description:

*Flower arrangement and flowering habit.*—Single flowers arranged in inversely conical umbels arising from apical leaf axils; umbels displayed above the foliar plane on strong peduncles; flowers face upright to mostly outwardly; freely flowering habit; about five flowers per umbel with about 40 umbels developing per plant.

*Fragrance.*—None detected.

*Flowering season.*—Early flowering habit, plants begin flowering about five months after planting; plants do not require a traditional cooling treatment for flower initiation and development; in the garden in Germany, plants flower during the spring and again during the summer.

*Flower longevity.*—Flowers last about two weeks on the plant; flowers not persistent.

*Umbel height.*—About 5.5 cm.

*Umbel diameter.*—About 8 cm.

*Flower diameter.*—About 4.5 cm.

*Flower depth (height).*—About 3 cm.

*Flower buds.*—Length: About 1.5 cm. Diameter: About 5 mm. Shape: Spindle-shaped. Color: Close to 146B.

*Petals.*—Quantity per flower: Five or six arranged in a single whorl; two or three upper and three lower petals; petals imbricate. Length, all petals: About 3 cm. Width, all petals: About 2.5 cm. Shape, all petals: Obovate. Apex, all petals: Rounded. Base, all petals: Cuneate. Margin, all petals: Entire; undulate. Texture, all petals, upper and lower surfaces: Smooth, glabrous; velvety. Color, all petals: When opening, upper surface: Close to 68B; towards the base, close to 155D. When opening, lower surface: Close to 68C; towards the base, close to 155D. Fully opened, upper surface: Close to 68C; towards the base, close to 155D; venation, close to 68C and 155D; main color becoming closer to 68D with development. Fully opened, lower surface: Close to 68D; towards the base, close to 155D; venation, close to 68D and 155D.

*Sepals.*—Quantity per flower: Five or six arranged in a single whorl. Length: About 1.4 cm. Width: About 5 mm. Shape: Lanceolate. Apex: Acute; somewhat reflexing. Margin: Entire. Texture, upper and lower surfaces: Pubescent. Color, upper and lower surfaces: Close to 146B.

*Peduncles (umbel stems).*—Length: About 4.5 cm. Diameter: About 2 mm. Strength: Strong; flexible. Texture: Pubescent. Color: Close to 146B.

*Pedicels (individual flower stems).*—Length: About 2.5 cm. Diameter: About 1 mm. Strength: Strong; flexible. Texture: Pubescent. Color: Close to 146B.

*Reproductive organs.*—Androecium: Stamen development not observed. Gynoecium: Pistil quantity per flower: One. Pistil length: About 1.5 cm. Stigma shape: Five or six-parted. Stigma color: Close to 61A.

Style length: About 7 mm. Style color: Close to 61B. Ovary color: Close to 147C. Seeds and fruits: Seed and fruit development have not been observed on plants of the new Regal Geranium.

Disease & pest resistance: Plants of the new Regal Geranium have not been observed to be resistant to pathogens and pests common to Regal Geranium plants.

Temperature tolerance: Plants of the new Regal Geranium have been observed to tolerate temperatures ranging from about 1° C. to about 35° C. to 40° C.

It is claimed:

1. A new and distinct Regal Geranium plant named 'REGBESOPI' as illustrated and described.

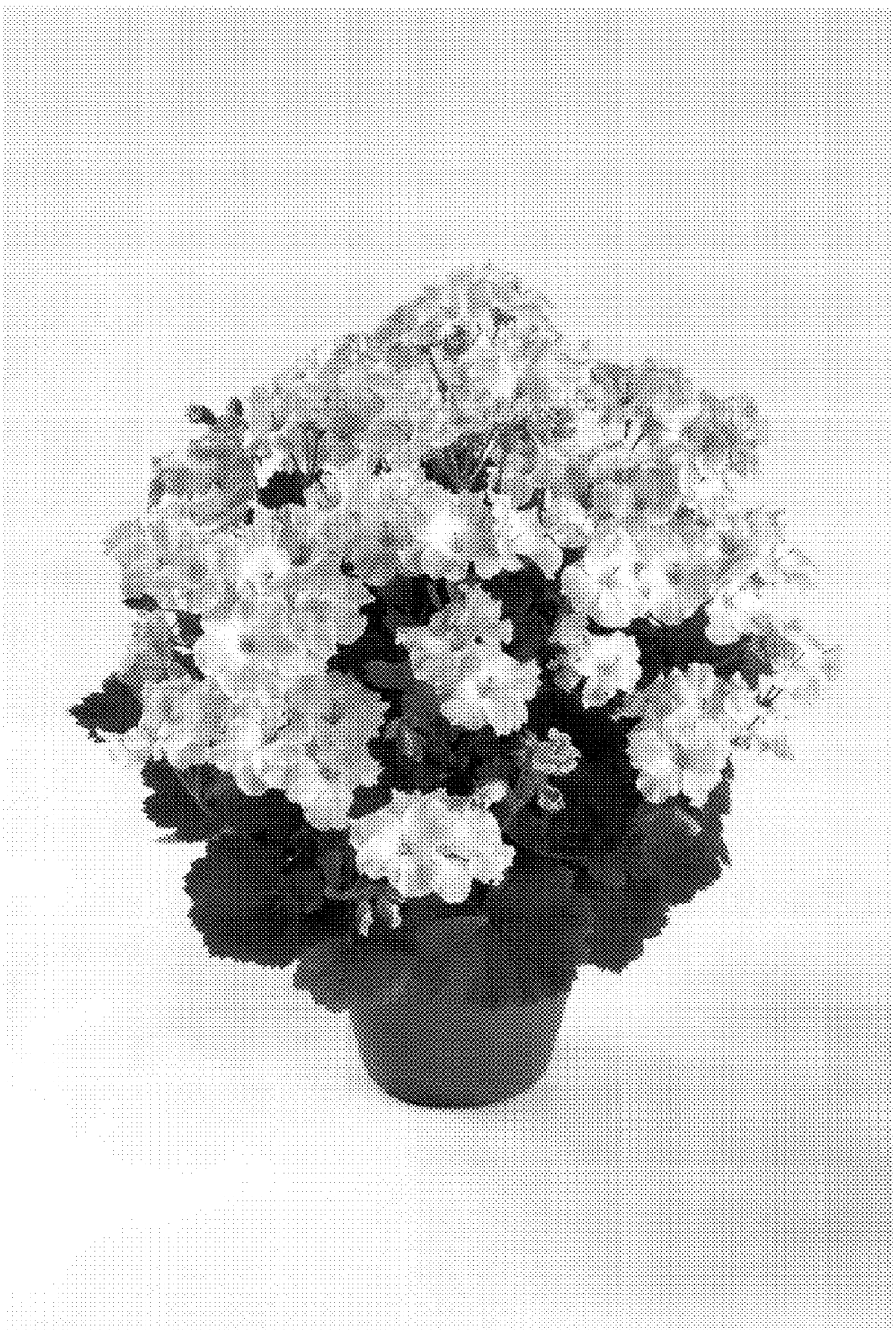

* * * * *